(12) United States Patent
Pham et al.

(10) Patent No.: US 11,147,596 B2
(45) Date of Patent: *Oct. 19, 2021

(54) SACRAL-ILIAC STABILIZATION SYSTEM

(71) Applicant: GLOBUS MEDICAL, INC., Audubon, PA (US)

(72) Inventors: Khiem Pham, Chalfont, PA (US); Mark Salzberger, Sinking Spring, PA (US)

(73) Assignee: Globus Medical, Inc., Audubon, PA (US)

( * ) Notice: Subject to any disclaimer, the term of this patent is extended or adjusted under 35 U.S.C. 154(b) by 186 days.

This patent is subject to a terminal disclaimer.

(21) Appl. No.: 16/448,610

(22) Filed: Jun. 21, 2019

(65) Prior Publication Data
US 2019/0307490 A1   Oct. 10, 2019

Related U.S. Application Data

(63) Continuation of application No. 13/189,084, filed on Jul. 22, 2011, now Pat. No. 10,368,919.

(60) Provisional application No. 61/366,815, filed on Jul. 22, 2010.

(51) Int. Cl.
*A61B 17/70* (2006.01)
(52) U.S. Cl.
CPC ...... *A61B 17/7055* (2013.01); *A61B 17/7032* (2013.01)

(58) Field of Classification Search
CPC .............. A61B 17/8057; A61B 17/809; A61B 17/7055; A61B 17/7059; A61B 17/8066; A61B 17/8061
See application file for complete search history.

(56) References Cited

U.S. PATENT DOCUMENTS

| | | | |
|---|---|---|---|
| 4,773,402 A | 9/1988 | Asher et al. | |
| 5,084,049 A | 1/1992 | Asher | |
| 5,127,912 A | 7/1992 | Ray | |
| 5,133,717 A * | 7/1992 | Chopin | A61B 17/7055 606/264 |
| 5,147,360 A | 9/1992 | Dubousset | |
| 5,300,073 A | 4/1994 | Ray | |
| 5,571,102 A | 11/1996 | Cavagna | |
| 5,622,652 A | 4/1997 | Kucherovsky | |
| 5,993,449 A | 11/1999 | Schlapfer et al. | |
| 6,106,526 A | 8/2000 | Harms | |
| 6,129,730 A | 10/2000 | Bono et al. | |
| 6,132,431 A | 10/2000 | Nilsson | |
| 6,187,005 B1 | 2/2001 | Brace et al. | |
| 6,197,028 B1 | 3/2001 | Ray | |
| 6,458,131 B1 | 10/2002 | Ray | |
| 6,485,491 B1 | 11/2002 | Farris | |
| 6,520,990 B1 | 2/2003 | Ray | |
| 6,648,885 B1 | 11/2003 | Friesem | |
| 6,682,532 B2 | 1/2004 | Johnson et al. | |

(Continued)

*Primary Examiner* — Julianna N Harvey

(57) ABSTRACT

The present invention provides a sacral-iliac plate having an iliac portion with a first screw hole for receiving a first fastener to secure the iliac portion to the iliac bone. A sacral portion integrated monolithically with the iliac portion is also provided with a second and third screw holes for receiving second and third fasteners to secure the sacral portion to the sacral bone. The sacral portion also includes a tulip for receiving and securing a spinal rod.

20 Claims, 5 Drawing Sheets

(56) References Cited

U.S. PATENT DOCUMENTS

| | | |
|---|---|---|
| 6,755,829 B1 | 6/2004 | Bono |
| 7,081,117 B2 | 7/2006 | Bono |
| 7,128,744 B2 | 10/2006 | Weaver et al. |
| 7,232,441 B2 | 6/2007 | Altarac |
| 7,303,563 B2 | 12/2007 | Poyner |
| 7,455,684 B2 | 11/2008 | Gradel |
| 7,575,588 B2 | 8/2009 | Barker |
| 7,699,872 B2 | 4/2010 | Farris |
| 7,850,719 B2 | 12/2010 | Gournay et al. |
| 8,007,499 B2 | 8/2011 | Piehl |
| 9,585,697 B2 | 3/2017 | Stachniak |
| 9,757,154 B2 | 9/2017 | Donner et al. |
| 9,872,711 B2 | 1/2018 | Haynes et al. |
| 10,368,919 B2 * | 8/2019 | Pham ................ A61B 17/7032 |
| 2004/0162558 A1 | 8/2004 | Hegde et al. |
| 2005/0015093 A1 * | 1/2005 | Suh .................... A61B 17/1728 606/96 |
| 2006/0106382 A1 | 5/2006 | Gournay et al. |
| 2006/0241615 A1 * | 10/2006 | Melkent ............. A61B 17/7044 606/281 |
| 2008/0021454 A1 | 1/2008 | Chao et al. |
| 2008/0125781 A1 | 5/2008 | Hoffman et al. |
| 2009/0125067 A1 | 5/2009 | Mazzuca et al. |
| 2010/0082067 A1 | 4/2010 | Kondrashov |
| 2010/0114177 A1 | 5/2010 | Piehl |
| 2012/0022595 A1 | 1/2012 | Pham et al. |
| 2014/0249581 A1 | 9/2014 | Stachniak |

\* cited by examiner

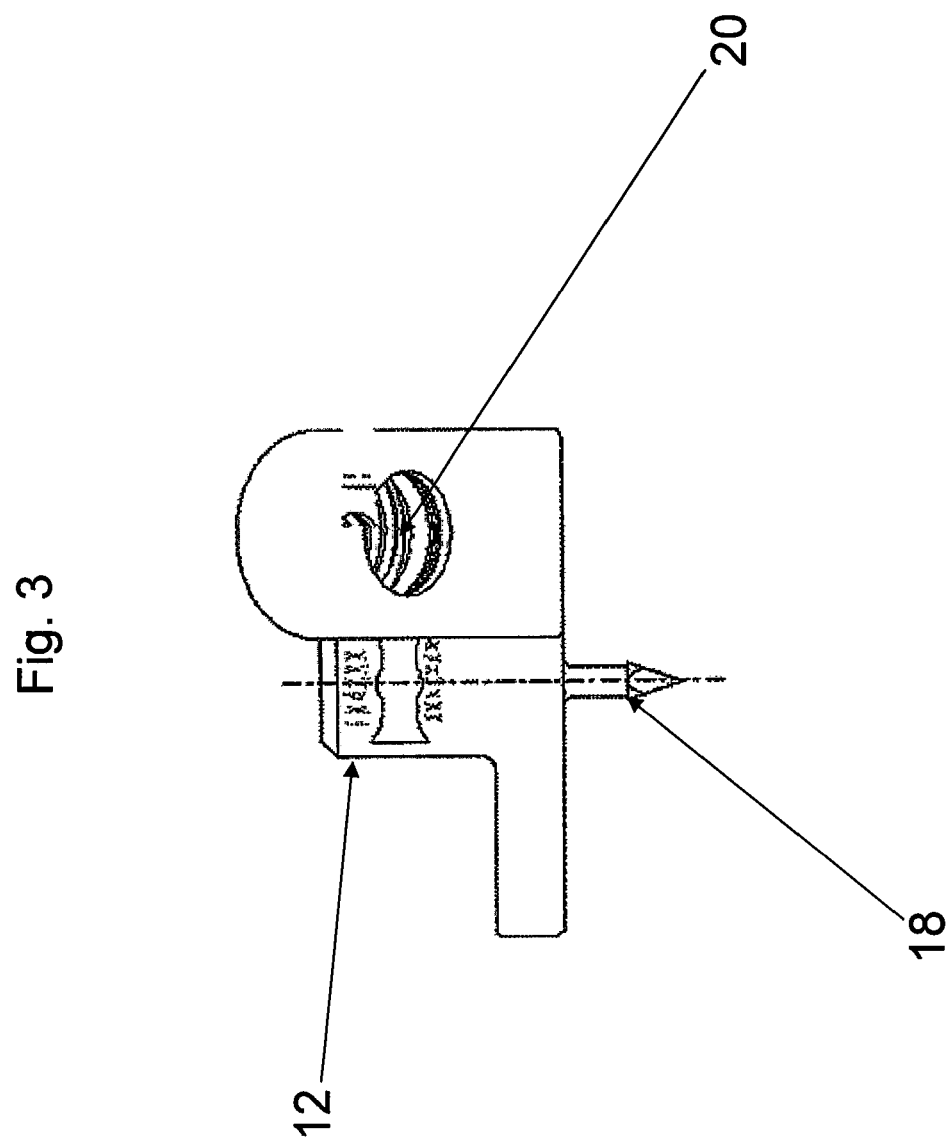

SACRAL-ILIAC STABILIZATION SYSTEM

CROSS REFERENCE TO RELATED APPLICATIONS

This application is a continuation application of U.S. Ser. No. 13/189,084, filed on Jul. 22, 2011 (published as U.S. Pat. Pub. No. 2012-0022595), which is a non-provisional application that claims priority to Provisional Application Ser. No. 61/366,815 filed on Jul. 22, 2010, all of which are incorporated herein in their entireties.

FIELD OF THE INVENTION

The present disclosure generally relates to a fixation device for positioning a plate between the sacrum and iliac portion of the human body.

BACKGROUND OF THE INVENTION

Bones and bony structures are susceptible to a variety of weaknesses that can affect their ability to provide support and structure. Weaknesses in bony structures may have many causes, including degenerative diseases, tumors, fractures, and dislocations. Advances in medicine and engineering have provided doctors with a plurality of devices and techniques for alleviating or curing these weaknesses. Typically, weaknesses in the spine are corrected by using devises that fuse one or more vertebrae together. There is a need stabilizing the iliac portion of the human body to the sacrum portion of the vertebrae to provide additional stability.

SUMMARY OF THE INVENTION

The present invention provides a sacral-iliac plate having an iliac portion with a first screw hole for receiving a first fastener to secure the iliac portion to the iliac bone. A sacral portion integrated monolithically with the iliac portion is also provided with a second and third screw holes for receiving second and third fasteners to secure the sacral portion to the sacral bone. The sacral portion also includes a tulip for receiving and securing a spinal rod.

BRIEF DESCRIPTION OF THE DRAWINGS

FIG. 3 is back view of the sacral-iliac plate illustrated in FIG. 1-3;

DETAILED DESCRIPTION OF THE ILLUSTRATED EMBODIMENTS

While it is apparent that the invention disclosed herein is well calculated to fulfill the objects stated above, it will be appreciated that numerous modifications and embodiments may be devised by those skilled in the art.

Figure 1:
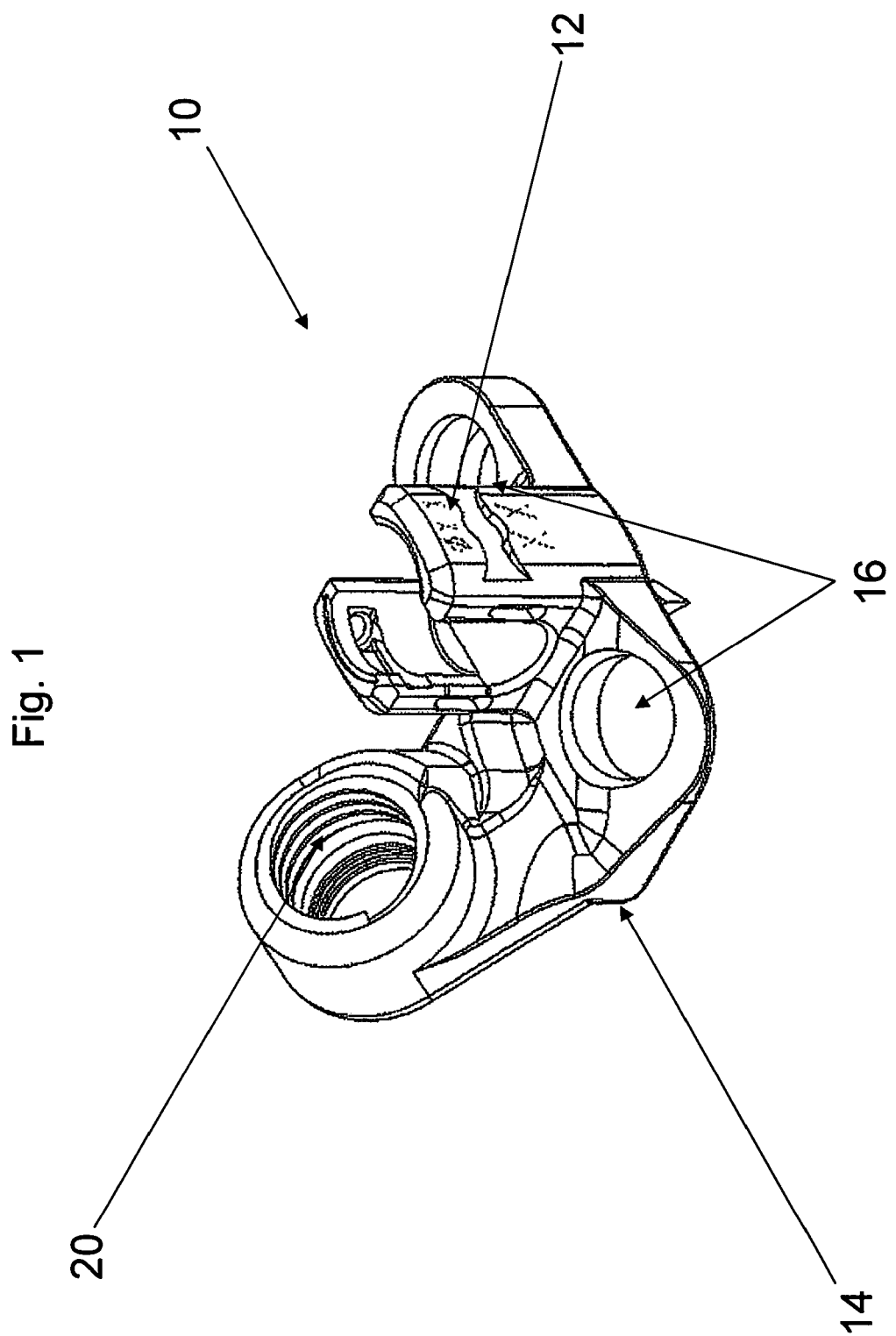
FIG. 1 is a perspective view of a sacral-iliac plate according to one embodiment of the present invention.

FIGS. 1-3 illustrate the sacral-iliac plate according to one embodiment of the present invention. Specifically, the sacral-iliac plate of the present invention enables surgeons the ability to use the plate for various medical conditions such as spondylolisthesis, neuromuscular scoliosis, degenerative lumbosacral joint, and pelvic obliquity.

Turning now to FIG. 1, a sacral-iliac plate 10 is shown. The plate 10 is a unitary plate with an integrated tulip 12 that provides support and stability across the sacral iliac joint configured to receive a spinal rod within the tulip 12. The plate 10 is further configured with an integrated tulip feature which allows the spinal rod to be top loaded.

Figure 2B:
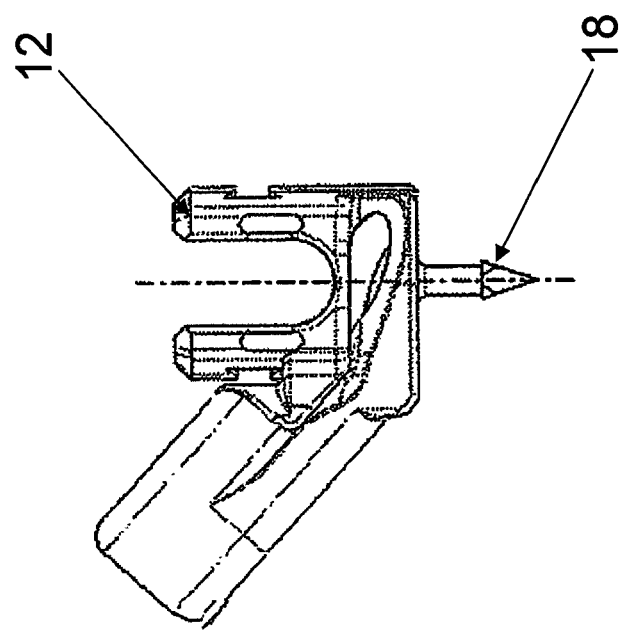
FIGS. 2A and 2B are side views of the sacral-iliac plate of the present invention.
Figure 2A:
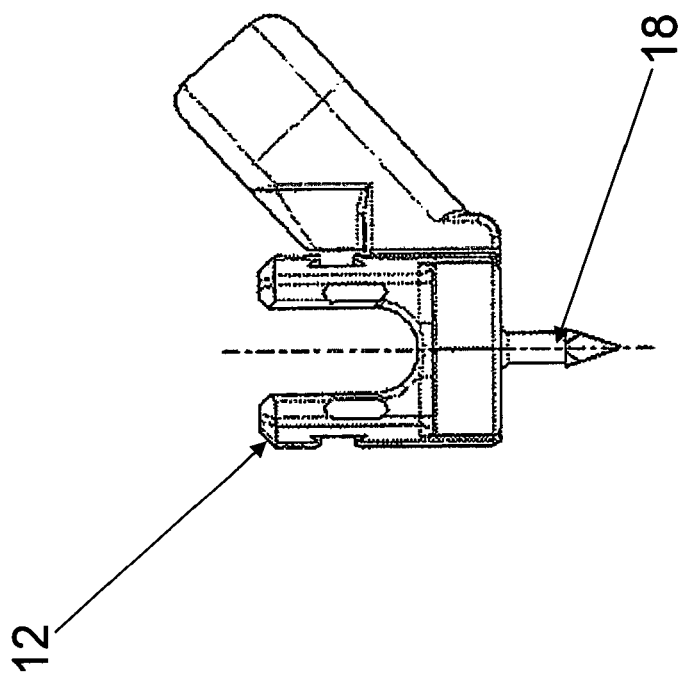

As best seen in the FIGS. 2A and 2B, the sacral iliac plate 12 includes a generally L-shaped body 14 with the integrated tulip head 12 interposed between and generally in line with two sacral holes 16. A sharp prong 18 or barb extends downward from the undersurface to facilitate temporary fixation during installation. The sacral holes 16 are non-threaded holes and are configured to receive screws there through to attach the sacral iliac plate to a sacrum bone of a patient. The tulip head 12 extends upward from the superior surface of the plate body 14 and forms a channel in the direction of the sacral holes 16 for receiving a spinal rod and a cap (not shown) may be used to secure the rod therein. In the embodiment illustrated, the sacral holes 16 are configured to be in-line with the tulip, however, the sacral holes 16 may be offset to accommodate the anatomy of the sacral bone. An iliac portion of the L-shaped body 14 extends laterally outward and angled upwards from a lower portion of the sacral iliac plate 12. The angulation of iliac portion of the plate 12 with respect to the lower portion is generally between 35° to 50° and preferably 40°.

The iliac portion has a threaded hole 20 that is configured to receive a screw therein to fix the iliac portion of the sacral iliac plate to the iliac bone of a patient. The iliac screw head has corresponding threads to mate with the threaded portion of the iliac screw hole 20. It should be noted that although in the present embodiment, the iliac portion of the plate 12 is provided with a threaded hole 20, a non-threaded hole may be utilized.

Figure 4:
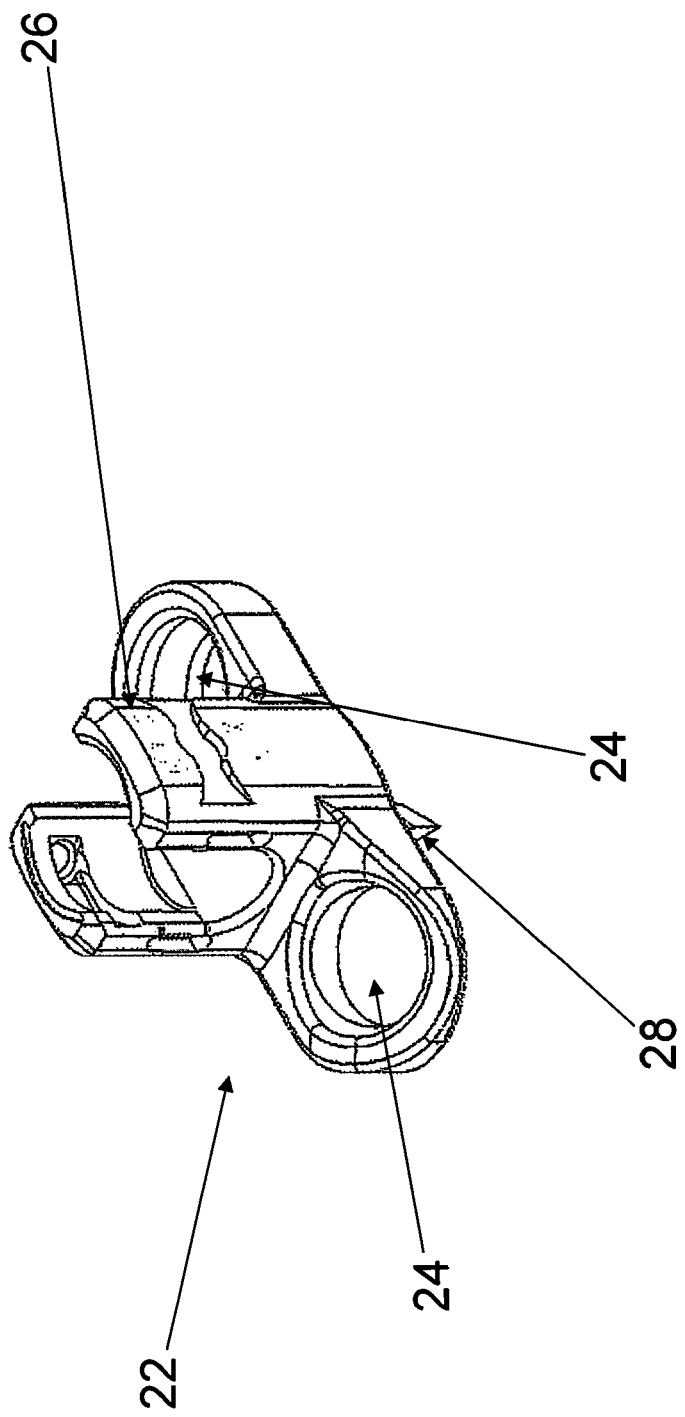
FIG. 4 is a perspective view of another embodiment of a sacral-iliac plate according to the present invention.
Figure 5B:
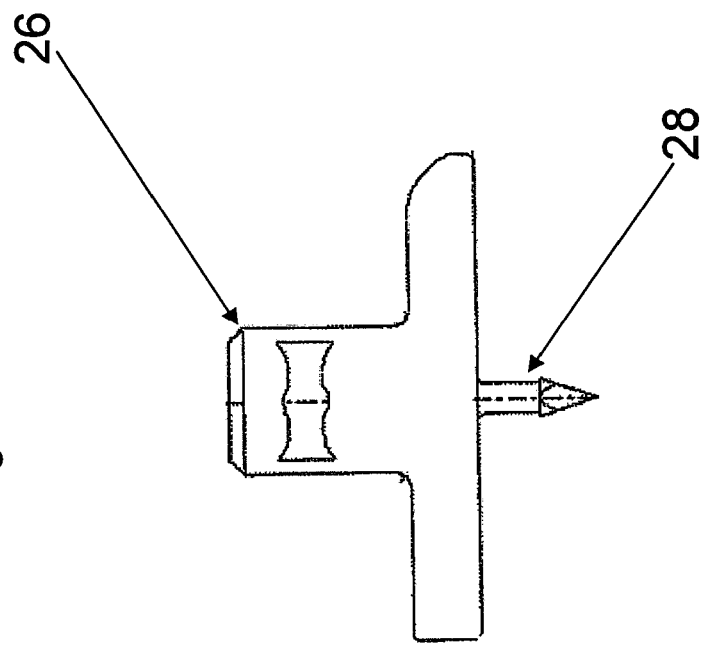
FIG. 5B is a side view of the sacral-iliac plate shown in FIG. 4.
Figure 5A:
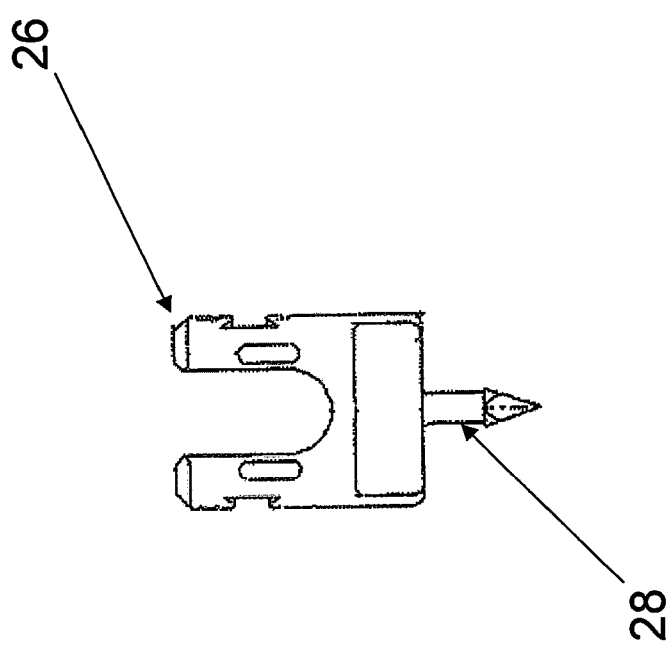
FIG. 5A is a front view of the sacral-iliac place shown in FIG. 4.

FIGS. 4, 5A and 5B illustrate another embodiment of the present invention. In this embodiment, the sacrum plate 22 is provided with two screw holes 24 having a tulip 26 configured between the two screw holes 24. The tulip 26 is designed and configured to receive a spinal rod and a locking cap. The plate is also provided with a sharp prong or barb 28 which extends downward from the undersurface to facilitate temporary fixation during installation. It should be noted that although a single prong is illustrated, multiple prongs may be used to more securely fixate the plate to the sacrum.

The various features and embodiments of the invention described herein may be used interchangeably with other feature and embodiments. Finally, while it is apparent that the illustrative embodiments of the invention herein disclosed fulfill the objectives stated above, it will be appreciated that numerous modifications and other embodiments may be devised by one of ordinary skill in the art. Accordingly, it will be understood that the appended claims are intended to cover all such modifications and embodiments which come within the spirit and scope of the present invention.

The invention claimed is:

1. A sacral-iliac plate comprising:
    an iliac portion having a first screw hole for receiving a first fastener to secure the iliac portion to the iliac bone; and
    a sacral portion integrated monolithically with the iliac portion having a second and third screw holes for receiving a second and third fasteners to secure the sacral portion to the sacral bone, wherein the sacral portion comprises a tulip for receiving and securing a spinal rod, wherein the tulip forms a channel for receiving the spinal rod, the channel extending at least partially along the length of the spinal rod towards the second and third screw holes, wherein the iliac portion is angled between 35° to 50° with respect to the sacral portion, wherein the sacral portion extends from a first end to a second end, wherein the sacral portion includes a first portion extending from the first end to a base of the tulip and a second portion extending from the second end to the base of the tulip, and wherein the first portion has a thickness that is less than a thickness of the second portion, wherein the thickness of the second portion is measured from the base of the tulip.

2. The sacral-iliac plate according to claim 1, wherein the sacral portion further comprises a prong extending downward from a bottom surface.

3. The sacral-iliac plate according to claim 1, wherein the second and third screw holes are in line with the tulip.

4. The sacral-iliac plate according to claim 1, wherein the tulip is interposed between the second and third screw holes.

5. The sacral-iliac plate according to claim 1, wherein the tulip is configured to secure the spinal rod with a locking cap.

6. The sacral-iliac plate according to claim 1, wherein the first screw hole is threaded.

7. The sacral-iliac plate according to claim 6, wherein the first screw hole is configured to mate with a threaded head of the first fastener.

8. The sacral-iliac plate according to claim 1, wherein the iliac portion is angled at 40° with respect to the sacral portion.

9. A sacral-iliac plate comprising:

an iliac portion having a first screw hole for receiving a first fastener to secure the iliac portion to the iliac bone; and a sacral portion integrated monolithically with the iliac portion having a second and third screw holes for receiving a second and third fasteners to secure the sacral portion to the sacral bone, wherein the sacral portion comprises a tulip for receiving and securing a spinal rod, wherein the tulip forms a channel for receiving the spinal rod, the channel extending at least partially along the length of the spinal rod towards the second and third screw holes, wherein the sacral portion extends from a first end to a second end, wherein the sacral portion includes a first portion extending from the first end to a base of the tulip and a second portion extending from the second end to the base of the tulip, wherein the first portion has a thickness that is less than a thickness of the second portion, wherein the thickness of the second portion is measured from the base of the tulip.

10. The sacral-iliac plate according to claim 9, wherein the sacral portion further comprises a prong extending downward from a bottom surface.

11. The sacral-iliac plate according to claim 9, wherein the second and third screw holes are in line with the tulip.

12. The sacral-iliac plate according to claim 9, wherein the tulip is interposed between the second and third screw holes.

13. The sacral-iliac plate according to claim 9, wherein the tulip is configured to secure the spinal rod with a locking cap.

14. The sacral-iliac plate according to claim 9, wherein the first screw hole is threaded.

15. The sacral-iliac plate according to claim 14, wherein the first screw hole is configured to mate with a threaded head of the first fastener.

16. The sacral-iliac plate according to claim 9, wherein the iliac portion extends laterally outward and is angled between 35° to 50° with respect to the sacral portion.

17. The sacral-iliac plate according to claim 9, wherein the iliac portion extends laterally outward and is angled at 40° with respect to the sacral portion.

18. A method of stabilizing a spine comprising:

accessing the sacrum and iliac portions of the spine;

positioning a sacral-iliac plate on a portion of the sacrum and a portion of the iliac bone; and securing the sacral iliac plate to the portion of the sacrum and the iliac bone;

wherein the sacral-iliac plate comprises:

an iliac portion having a first screw hole for receiving a first fastener to secure the iliac portion to the iliac bone; and a sacral portion integrated monolithically with the iliac portion having a second and third screw holes for receiving a second and third fasteners to secure the sacral portion to the sacral bone, wherein the sacral portion comprises a tulip for receiving and securing a spinal rod, wherein the tulip forms a channel for receiving the spinal rod, the channel extending at least partially along the length of the spinal rod towards the second and third screw holes, wherein the sacral portion extends from a first end to a second end, wherein the sacral portion includes a first portion extending from the first end to a base of the tulip and a second portion extending from the second end to the base of the tulip, wherein the first portion has a thickness that is less than a thickness of the second portion, wherein the thickness of the second portion is measured from the base of the tulip.

19. The method according to claim 18, wherein the sacral-iliac plate includes a prong extending downward from a bottom surface of the sacral portion for additional fixation.

20. The method according to claim 18, wherein the sacral-iliac plate includes the iliac portion angled 40° with respect to the sacral portion.

* * * * *